United States Patent [19]

Chang et al.

[11] Patent Number: 5,418,140
[45] Date of Patent: May 23, 1995

[54] **RAPID IDENTIFICATION OF *VIBRIO PARAHAEMOLYTICUS* FROM FOODS**

[75] Inventors: Tsung C. Chang, Taoyuan; Hui C. Chen, Miaoly, both of Taiwan, Prov. of China

[73] Assignee: Food Industry Research and Development Institute,

[21] Appl. No.: 104,880

[22] Filed: Aug. 10, 1993

[51] Int. Cl.$^6$ .......................................... G01N 33/569
[52] U.S. Cl. .................................. 435/7.32; 435/975; 436/534; 436/547; 436/548; 530/389.5; 530/391.1; 530/825
[58] Field of Search ............... 435/7.32, 975; 436/533, 436/534, 547, 548; 530/388.4, 389.5, 391.1, 825

[56] References Cited

PUBLICATIONS

Chen et al, "Rapid Detection of *Vibrio parahaemolyticus* in Food by Immunofluorescence Microscopy", Abstract P-14, 93rd ASM General Meeting held 16–20 May 1993.

L. B. Bangs, Uniform Latex Particles, pp. 47–58, 61–64 (Seradyn Inc., Indianapolis, Ind., 1984).
Koga et al, "Isolation and Characterization of the Outer Membrane from *Vibrio parahaemolyticus*" J. Gen. Microbiol., 129: 3185–3196 (1983).
S. Kabir, "Composition and Immunochemical Properties of Outer Membrane Proteins of *Vibrio cholerae*", J. Bacteriol., 144(1): 382–389 (Oct. 1980).

*Primary Examiner*—Carol E. Bidwell
*Attorney, Agent, or Firm*—Fish & Richardson

[57] ABSTRACT

A method for rapid identification of *Vibrio parahaemolyticus* in a sample containing suspect colonies which includes the steps of:
(i) coating latex particles with a solution of antibodies or antisera against outer membrane proteins of *V. parahaemolyticus* at an appropriate concentration to obtain a latex reagent, and
(ii) mixing the sample with the latex reagent obtained in the (i) under conditions appropriate to complete agglutination; and a kit for accomplishing the method are disclosed.

2 Claims, 2 Drawing Sheets

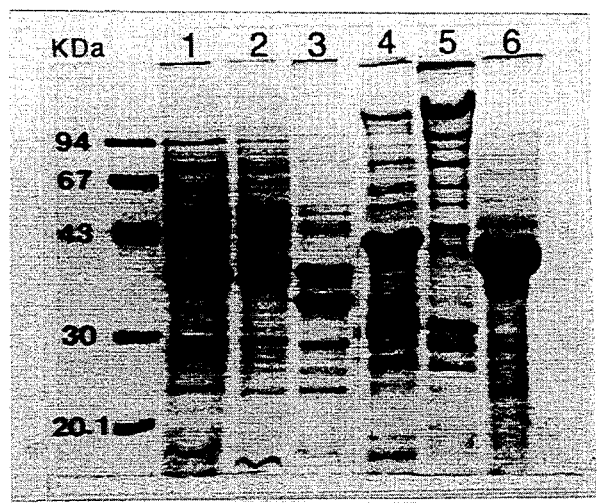
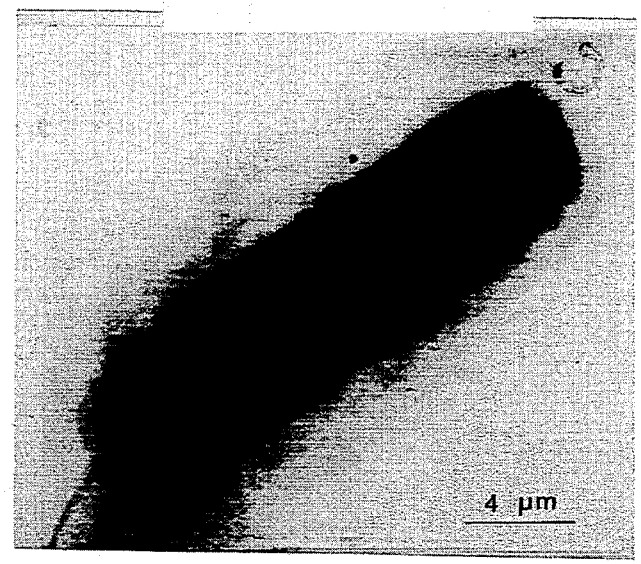
FIG. 2A
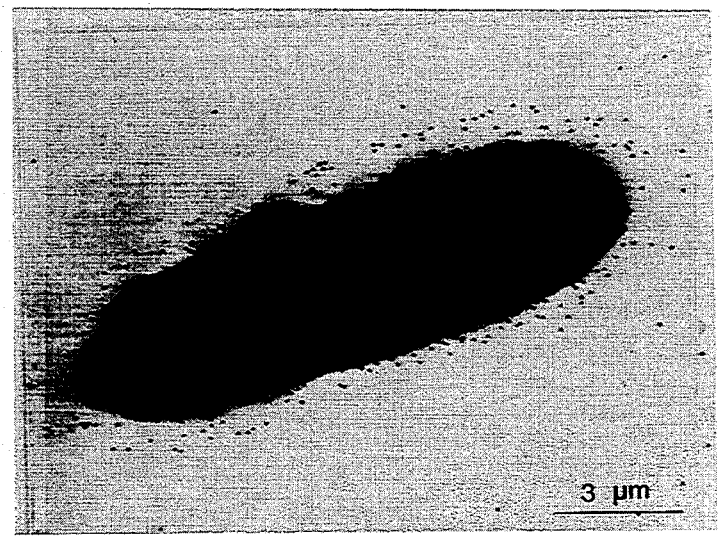
FIG. 2B

RAPID IDENTIFICATION OF *VIBRIO PARAHAEMOLYTICUS* FROM FOODS

FIELD OF THE INVENTION

The present invention relates to a method for rapid identification of *Vibrio parahaemolyticus*, and more particularly, to a latex agglutination test for identification of *V. parahaemolyticus* using antibodies or antisera against the outer membrane proteins of the bacterium.

BACKGROUND OF THE INVENTION

*Vibrio parahaemolyticus* is a halophilic, Gram-negative, facultative anaerobic microorganism occurring in most of the estuarine waters of the world. It causes food poisoning associated with the consumption of seafoods and is the major bacterial cause of epidemic gastroenteritis in the countries where fish are eaten raw, such as Japan and Taiwan.

The conventional methods for the identification of *V. parahaemolyticus* are based on morphological, biochemical and physiological tests. These tests are tedious, time-consuming, cumbersome and costly. It normally takes several days to complete such tests, and thus the clearance of highly perishable foods is delayed. Therefore, a rapid and specific identification test for the suspect colonies is desirable, for example, a latex agglutination test.

Chang et al. in Chinese (Taiwan) Patent Application No. 79109870, Pat. No. NI-50873 published on 21 Aug. 1991 (1) disclosed a latex agglutination test for identification of the colonies of *Vibrio*. The latex agglutination test is characterized by coating the latex particles with antibodies against capsule antigens of *V. parahaemolyticus* wherein the antibodies were raised by immunizing rabbits with mixed capsule antigens of 13 strains of *V. parahaemolyticus* and the cross-reaction with the Aeromonas species was reduced by absorption of said antibodies with Aeromonas media.

However, it is found in this invention that the outer membrane proteins of *V. parahaemolyticus*, especially with molecular weights of 36,000 and 34,000, respectively, are highly antigenic and specific to *V. parahaemolyticus*. The invention provides a rapid identification of *V. parahaemolyticus* using the antibodies against the proteins.

The method of the invention is very simple and economical and can be completed within minutes. The invention provides a rapid identification of *V. parahaemolyticus* with high sensitivity and specificity, and low (less than 5%) false-negative and false-positive rates.

SUMMARY OF THE INVENTION

Accordingly, it is an object of the invention to provide a method for rapid identification of *V. parahaemolyticus* in a sample containing suspect colonies which comprises the following steps of:

(i) coating latex particles with a solution of antibodies or antisera against outer membrane proteins of *V. parahaemolyticus* at an appropriate concentration to obtain a latex reagent, and (ii) mixing said sample with said latex reagent obtained in step (i) under conditions appropriate to complete agglutination.

Preferably, the antibodies or antisera against two outer membrane proteins of *V. parahaemolyticus* with molecular weights of 36,000 and 34,000, respectively, are used.

It is another object of the present invention to provide a kit for rapid identification of *V. parahaemolyticus* comprising latex particles coated with antibodies or antisera against outer membrane proteins of *V. parahaemolyticus* in association with reagents and devices required for establishing a latex agglutination test.

These and other objects, advantages and features of the present invention will be more fully understood and appreciated by reference to the written specification.

BRIEF DESCRIPTION OF THE DRAWINGS

FIG. 1 is the patterns of sodium dodecyl sulfate polyacrylamide gel electrophoresis (SDS-PAGE) of outer membrane proteins purified from three strains of *V. parahaemolyticus* and three strains of other Vibrio spp: the unnumbered lane, molecular weight markers; lanes 13–3, the outer membrane protein patterns of *V. parahaemolyticus* CCRC 10806, 12866 and 12966, respectively; lane 4, that of *V. marinofulvus* CCRC 13863; lane 5, that of *V. ponticus* CCRC 13867; and lane 6, that of *V. cholerae* CCRC 14143.

FIGS. 2A–2D show immunoelectron micrographs of *V. parahaemolyticus* and *V. cholerae* labeled with preimmune serum or antibodies against the outer membrane proteins with molecular weights of 36,000 and 34,000, respectively, and then labeled with protein A-colloidal gold (particle size 10 nm):

FIG. 2A is a micrograph of a negative control;

FIG. 2B is a micrograph of *V. parahaemolyticus* CCRC 10806 labeled with antibodies and protein A-colloidal gold;

FIG. 2C is a micrograph of *V. parahaemolyticus* CCRC 10806 labeled with antibodies and protein A-colloidal gold; and FIG. 2D is a micrograph of *V. cholerae* CCRC 14143 labeled with antibodies and protein A-colloidal gold.

DETAILED DESCRIPTION OF THE INVENTION

Figure 2C:
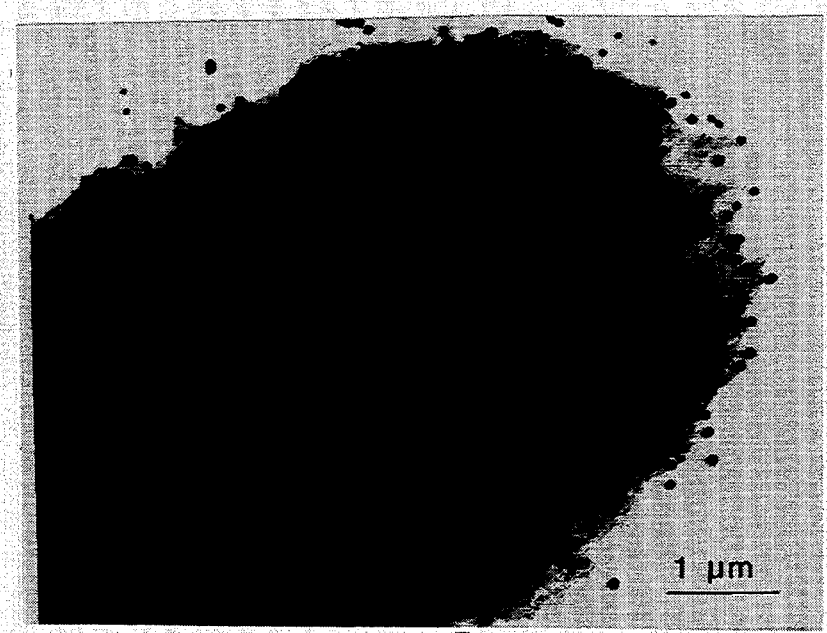

As used herein, the term "rapid identification" refers to a test for identification of a specific bacterium completed within several minutes. It takes several days to complete an identification of *V. parahaemolyticus* by conventional methods. However, the method of the invention can be completed within several minutes. In an embodiment of the invention, it takes only about 2 minutes.

The term "latex agglutination test" as used herein refers to a test in which reactions between antigens (e.g. bacterial proteins) and latex particles coated with antibodies are detected by agglutination.

As used herein, the term "antibody" refers to any immunoglobulin molecule produced by an animal in direct response to an antigen, and which can combine specifically, non-covalently with the antigen which elicited its formation. Normally, the antibodies are raised by immunizing animals such as rabbits, goats and sheep with the antigen emulsified with an adjuvant. The term "antisera" refers to the blood rich in the desired antibodies from the immunized animals.

The term "outer membrane proteins of *V. parahaemolyticus*" as used herein refers to the proteins at the outer membrane area of *V. parahaemolyticus*. It is known that the outer membranes of Gram-negative bacteria contain several distinct proteins with molecular weights in the range of 30,000–40,000. These proteins have been isolated and characterized. They are reported to be species-specific and with high antigenicity by Kabir (7, 8). Kabir's reports are incorporated by reference. The invention utilizes the against the proteins as tools to provide a rapid identification of V. parahaemolyticus.

According to the invention, the outer membrane of V. parahaemolyticus was analyzed by electrophoresis and found to contain two major proteins with molecular weights of 36,000 and 34,000, respectively. The natures of these two proteins are not comprehended in detail; however, it is known that these two proteins represent about one third of the amount of total outer membrane proteins (FIG. 1, lane 1, as indicated by arrows).

The outer membrane proteins of V. parahaemolyticus can be purified by conventional procedures, such as that described by Koga and Kawata (9), which reference is incorporated by reference. In a preferable embodiment of the invention, the outer membrane proteins of V. parahaemolyticus are separated by sodium dodecyl sulfate polyacrylamide gel electrophoresis (SDS-PAGE), and the desired bands are cut directly from the SDS gel. This is a convenient and expedient way to obtain highly purified proteins for immunization purposes.

The preparation of the antisera or antibodies against the outer membrane protein and their purification can be followed by standard procedures known to those skilled in the art. The outer membrane proteins are used as immunogens and the animals are immunized by the polyacrylamide gel ground to very fine particles containing the outer membrane proteins. The procedure eliminates the step of eluting proteins from the gel and hence avoids further loss of the proteins. In addition, polyacrylamide gel was reported to have the same effect as an adjuvant by slowly releasing proteins from the gel (2, 13), which references are incorporated by reference. Although the antigens used for immunization were denatured proteins (due to SDS-PAGE), the antibodies still recognized the native outer membrane proteins as demonstrated by electron microscopy (FIG. 2) and latex agglutination (Table 1). This might be due to the polyclonal properties of the antibodies which could still react with some epitopes of the native proteins.

The samples to be tested can be enriched and then streaked on selective agar plates to obtain suspect colonies. According to the conventional techniques (6), samples are commonly enriched either in alkaline peptone water or in salt polymyxin B broth followed by streaking on a selective agar medium (e.g. thiosulfate-citrate-bile salts-sucrose agar, TCBS). For instance, said suspect colonies grown on TCBS are then analyzed by the method of the invention.

The latex agglutination test 0f the invention is carried out by standard procedures know to those skilled in the art. The latex particles can be colored particles, e.g. yellow in color, rendering the agglutination clumps very easy to observe. The latex particles are previously sensitized with antibodies by incubating the particles with a solution of the purified antibodies. The concentration of the solution with antibodies depends upon the titer of the antibodies and manufacturers' needs. An appropriate concentration of the solution for sensitization can be readily determined by those skilled in the art; for instance, 70 µg/ml in an embodiment of the invention. The sensitization of latex particles includes the steps of washing the latex particles with a buffer such as phosphate buffer, incubating the washed latex particles with a solution of the purified antibodies in a buffer such as phosphate-buffered saline, and removing unbound antibodies by centrifugation and then washing the latex with a buffer containing blocking proteins such as bovine serum albumin (BSA). The solution containing the latex particles coated with the antibodies is used as a latex reagent for the agglutination test.

In an embodiment of the invention, the latex agglutination test is performed on a microscope slide. There may be two circles (about 1.5 cm diameter) marked with a wax pencile on a slide in which one is for the latex reagent (containing latex particles coated with antibodies) and the other is -for the control latex reagent (containing latex particles coated with normal rabbit IgG). The suspect colonies are transferred to each circle on the slide and the control latex (sensitized with normal rabbit IgG) in a solution is added to one circle, and the test latex (sensitized with antibodies) is added to the other circle. The contents are completely mixed with a toothpick and gently rocked back and forth for about 1 min. When agglutination is observed in the circle containing test latex while the latex in the control circle still remains homogeneous, the reaction is positive. On the other hand, the reaction is negative when no agglutination is observed in both circles.

The method for rapid identification of V. parahaemolyticus in a sample containing suspect colonies of the invention encompasses the following steps:
(i) coating latex particles with a solution of antisera or antibodies against outer membrane proteins of V. parahaemolyticus at an appropriate concentration to obtain a latex reagent, and
(ii) mixing said sample with said latex reagent obtained in step (i) under conditions appropriate to complete agglutination.

The sensitivity as high as up to 98.9% of the method of the invention can be obtained. The high sensitivity suggests the presence of these common proteins on the cell surface of V. parahaemolyticus. Although various strains of V. parahaemolyticus cover a wide range of serotypes, the latex agglutination test is species-specific rather than serotype-specific. The specificity of the method is higher than 90%, and the false-positive and false-negative rates are low, less than 5%. Autoagglutination rate is low (less than 3%) which is likely due to the cell surface characteristics of some bacteria. The invention provides an effective method for rapid identification of V. parahaemolyticus with good results.

EXAMPLE

Media and Strains

Tryptic soy argar (TSA), tryptic soy broth (TSB) and thiosulfate-citrate-bile salts-sucrose (TCBS) agar were purchased from Difco Laboratories (Detroit, Mich., USA).

All strains used for the latex agglutination tests according to the invention were 18 to 24 hours fresh cultures, including 94 isolates of V. parahaemolyticus, 40 isolates of other vibrios (21 species) and 39 strains (33 species) of other bacteria. Most of these bacteria were obtained from the Culture Collection and Research Center (CCRC, Hsinchu, Taiwan). Among the 94 isolates of V. parahaemolyticus, 60 were isolated from various seafoods and identified as V. parahaemolyticus by the methods described by Joseph et al. (6), which reference is incorporated by reference.

V. parahaemolyticus, V. alginolyticus, V. algosus, V. carchariae, V. harveyi and V. ponticus were grown on TSA with 3% NaCl (TSA-3% NaCl) at 35° C. for 18–24 hours. *V. anguillarum, V. diazotrophicus, V. fischeri, V. liquefaciens, V. marinagilis, V. ordalii, V. pelagius, V. tubiashii* and *V. vulnificus* were grown on TSA with 1.5% NaCl (TSA-1.5% NaCl) at 35° C. for 18–24 hours. *V. cholerae, V. costicola, V. fluvialis, V. minicus, V. percolans, V. salmonicida* and other non-vibrios were grown on TSA at 35° C. for 18–24 hours.

The strain used for purification of outer membrane proteins for immunization purpose was *V. parahaemolyticus* CCRC 10806 from the Culture Collection and Research Center (CCRC), Taiwan, which was grown in TSB with 3% NaCl (TSB-3% NaCl) at 35° C. for 12 hours.

Purification of Outer Membrane Proteins

The purification procedure was a modification of that described by Koga and Kawata (9), which reference is incorporated by reference. Briefly, a loop of overnight culture of *V. parahaemolyticus* was inoculated into 500 ml of TSB-3% NaCl and incubated for 12 hours at 35° C. in a gyratory shaker. The cells were harvested by centrifugation at 3,000×g for 15 min. at 4° C., and washed twice with 0.1M Tris-HCl buffer, pH 7.8. After centrifugation, the cell pellet was suspended in 10 ml of 0.1M Tris-HCl buffer, pH 7.8, and treated for 6 min. at 4° C. with a sonicator (Model W-375, Heat Systems Ultrasonic, New York, USA) setting at 200 W. Unbroken cells were removed by centrifugation at 3,000×g for 15 min. at 4° C. The cell envelopes were recovered from the supernatant by centrifugation at 30,000×g (PR83T rotor, Hitachi, Tokyo., Japan) for 30 min. at 4° C. The pellet was washed twice with 0.1M Tris-HCl buffer, pH 7.8, with a centrifugation step (30,000×g for 30 min. at 4° C.) after each washing. The inner cell membranes were removed from the envelopes by treating the pellet with 10 ml of 2% TRITON ™ X-100 (Sigma, St. Louis, Mo. USA) at room temperature for 1 hour. The suspension was centrifuged again (30,000×g, for 30 min. at 4° C.), and the pellet containing the outer membrane fraction was washed twice with the same Tris-HCl buffer and extracted with 10 ml of 2% sodium dodecyl sulfate (SDS) at 100° C. for 30 min. The total outer membrane proteins were obtained by centrifugation of the SDS-treated samples at 30,000×g for 30 min. at 4° C., and were used for subsequent electrophoresis and purification. Outer membrane proteins of several other vibrios were purified in a similar way. Protein content was measured according to the method of Lowry et al. (11), which reference is incorporated by reference.

Electrophoresis

Analytical SDS polyacrylamide gel electrophoresis (SDS-PAGE) was conducted with 10% gels having a thickness of 0.75 mm. The outer membrane protein patterns of 3 strains of *V. parahaemolyticus* and several Vibrio spp. are shown in FIG. 1. The outer membrane proteins purified from *V. parahaemolyticus* CCRC 10806, 12866 and 12966 as previously described were loaded to lanes 1, 2 and 3, respectively; that of *V. marinofulvus* CCRC 13863 to lane 4; that of *V. ponticus* CCRC 13867 to lane 5; and that of *V. cholerae* CCRC 14143 to lane 6. After electrophoresis, gels were stained with Commassie brilliant blue.

The protein patterns of *V. parahaemolyticus* were very similar, with 3 to 4 major bands having molecular mass in the range of 30,000 to 40,000 daltons (FIG. 1, lanes 1–3). Two distinct bands (indicated with arrows) with apparent molecular weights of 36,000 and 34,000, respectively, were abundant (FIG. 1, lanes 1–3). The outer membrane proteins of other Vibrio spp. were also shown in FIG. 1 (lanes 4–6); however, the patterns were quite different from those of *V. parahaemolyticus*. From the SDS-PAGE patterns, it was estimated that the abundance of the 36,000-Da protein was higher than the 34,000-Da protein and the two proteins represented as high as one third of the amount of total extracted outer membrane proteins.

For preparative purposes, about 2.8 mg of total outer membrane proteins was loaded onto each slab (3 mm thick). After separation of the outer membrane proteins, the protein bands were visualized by immersing the gels in 4M sodium acetate at room temperature for 10–20 min. with a gentle shaking (4), which reference is incorporated by reference. The two major outer membrane proteins with molecular weights of 36,000 and 34,000, respectively, were collectively cut from the preparative SDS gels (3 mm thick) and used as antigens for immunization.

Preparation of Antisera

The polyacrylamide gel strip containing the two outer membrane proteins (about 1 mg) was cut into small pieces, ground to fine particles with a hand homogenizer, and emulsified with 5 ml of incomplete Freund's adjuvant. Two New Zealand White rabbits (each 2.5 kg in weight) were used for immunization. Each rabbit was immunized subcutaneously at several sites on the back with 2 ml of the emulsified antigens and boosted 4 times at 3-week intervals in the same manner. Ten days after the final injection, blood was collected from the ears. The antisera from the collected blood were decomplemented by heating in a 56° C. water bath for 30 min., and the immunoglobulin G (IgG) fraction was obtained by ammonium sulfate fractionation and purified by diethylaminoethyl (DEAE) ion-exchange chromatography as described by Linn et al. (10), which reference is incorporated by reference.

The titer of the antisera was determined by an enzyme-linked immunosorbent assay (ELISA) with total outer membrane proteins (5 μg/ml) as the coating materials of microtitration plate and protein A-horseradish peroxidase conjugate as the signal producer of antigen-antibody reaction. The titer of the antisera after 4 boosts was around $1 \times 10^7$ as determined by the ELISA.

Affinity Purification of Antibodies

The total outer membrane proteins (112 mg) were immobilized on 5 g of cyanogen-bromide activated Sepharose 4B gel (Pharmacia, Uppsala, Sweden) according to the procedure as described by Hudson and Hay (5), which reference is incorporated by reference. The gel after coupling was packed into a column (1×22 cm) and equilibrated with phosphate-buffered saline (PBS, 0.01M sodium phosphate buffer, 0.14M NaCl, pH 7.2). The DEAE-purified IgG (45 mg) was loaded, and then the unbound proteins were washed away with PBS. The antibodies against the outer membrane proteins having molecular weights of 36,000 and 34,000, respectively, were eluted with 0.1M glycine-HCl buffer, pH 2.6, and immediately neutralized with 1M Tris-HCl buffer, pH 8.5.

Immunoelectron Microscopy

The procedure was a modification of that described by Fuerst and Perry (3), which reference is incorporated by reference. The cells of the overnight cultures of *V. parahaemolyticus* CCRC 10806 and *V. cholerae* CCRC 14143 were grown in TSB-3% NaCl and TSB, respectively, for 6 hours at 35° C. with shaking. Unlike the above step, the following procedures were performed at room temperature. The culture broth was centrifuged (3,000×g, 15 min.) and the pellet was resuspended and fixed in 1% glutaraldehyde for 5 min. Then the cells were centrifuged and washed twice with PBS, and resuspended in PBS to an absorbance of about 0.7 at 540 nm. A drop (25 µl) of this suspension was placed on a sheet of PARAFILM TM (American National Can, Greenwich, Conn., USA). A formvar-coated nickel grid was placed face down on the cell suspension for 2 min. The grid was recovered and excess solution was removed by holding the edge of the grid against a filter paper. The grid with the specimen on it was transferred sequentially onto drops of the following reagents on the same Parafilm sheet: PBS-0.2M glycine for 5 min., PBS-2% bovine serum albumin (BSA) for 5 min., affinity-purified antibodies diluted in PBS-2% BSA for 30 min., 5 washes in PBS-0.05% TWEEN TM 20, and protein A gold (Sigma, P-1039, particle size 10 nm) diluted 1:100 in PBS-2% BSA for 30 min. The grid was vigorously agitated in a beaker containing PBS-0.05% TWEEN TM 20, air dried, and observed under an electron microscope (Model H-600, Hitachi, Tokyo, Japan). The negative control was performed in a similar way, except that preimmune serum instead of the antibodies was used.

Figure 2D:
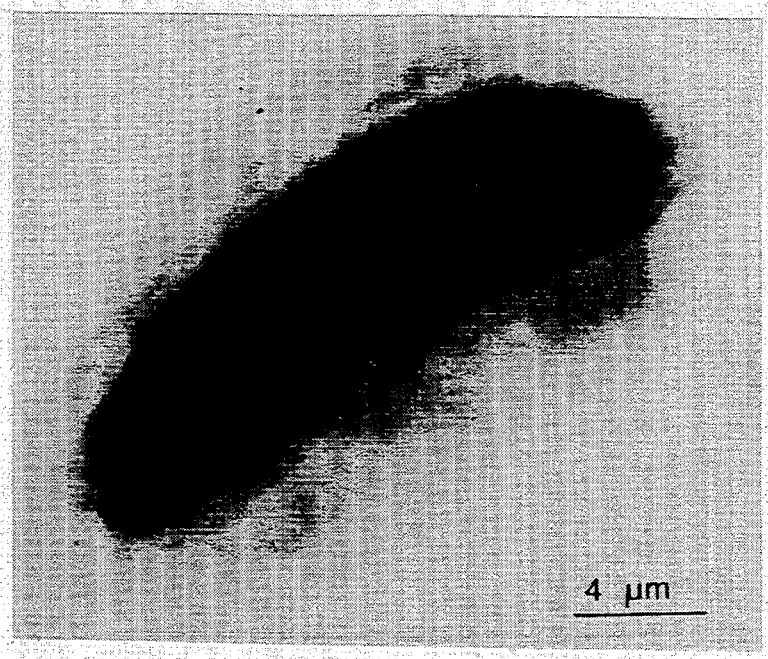

The electron micrographs of *V. parahaemolyticus* CCRC 10806 labeled with preimmune serum, *V. parahaemolyticus* CCRC 10806 and V. cholerae CCRC 14143 labeled with antibodies are shown in FIG. 2. Using protein A-gold as an immunolabeling signal, the proteins with 36,000 and 34,000 daltons were heavily labeled at the outer membrane area of *V. parahaemolyticus* (FIG. 2B and 2C) while very low levels of labeling were found in the negative control (FIG. 2A) and in *V. cholerae* (FIG. 2D). The results suggested that the outer membrane proteins with molecular weights of 36,000 and 34, 000 were on the cell surface of *V. parahaemolyticus*.

Sensitization of Latex

One milliliter of 10% latex (diameter 1.09 µm, Japan Synthetic Rubber, Tokyo, Japan) was washed two times with PBS and suspended in 20 ml of PBS. To the washed latex suspension, 20 ml of affinity-purified antibodies (70 µg/ml) was added and incubated at room temperature for 1 hour on an end-over-end mixer. The suspension was centrifuged in a swing bucket rotor (1,500×g for 15 min. at room temperature) to remove unbound antibodies, washed twice with PBS, and resuspended in 20 ml of PBS containing 0.5% BSA and 0.05% sodium azide. Control latex was coated in the same manner except that preimmune serum IgG was used for sensitization. The final concentration of latex reagent was 0.5% (w/v).

Latex Agglutination Test

On a microscope slide, 2 circles with an approximate diameter of 1.5 cm were marked with a wax pencil. One to two colonies grown overnight on TSA (or TSA with 1.5 or 3% NaCl) were transferred to each circle on the slide by a sterile toothpick. One drop (25 µl, approximately 2×10⁸ latex beads) of control latex was added to one circle, and one drop of test latex (sensitized with antibodies) was added to the other circle. The contents were smeared with the toothpick and gently rocked back and forth for 1 min. A positive reaction was recorded if agglutination was observed in the circle containing test latex, while the latex in the control circle still remained homogeneous. The reaction was recorded as negative if no agglutination was observed in both circles. Occasionally, autoagglutination was observed in both circles and it was recorded as "uninterpretable". *Escherichia coli* CCRC 10316 was used as a negative control.

The reactions of individual organisms with the latex reagent of the invention are shown in Table 1.

TABLE 1

Reactions of individual organisms with latex agglutination test

| Bacteria | No. of Strains | | |
|---|---|---|---|
| | Total | Positive | Negative |
| *V. parahaemolyticus* | 94 | 93 | 1 |
| *V. alginolyticus* | 2 | 1 | 1 |
| *V. algosus* | 1 | 0 | 1 |
| *V. anguillarum* | 2 | 0 | 2 |
| *V. carchariae* | 1 | 0 | 1 |
| *V. cholerae*[a] | 4 | 0 | 3 |
| *V. costicola* | 2 | 0 | 2 |
| *V. diazotrophicus* | 1 | 0 | 1 |
| *V. fischeri*[a] | 2 | 0 | 1 |
| *V. fluvialis* | 1 | 0 | 1 |
| *V. harveyi* | 2 | 1 | 1 |
| *V. liquefaciens* | 1 | 0 | 1 |
| *V. marinagilis* | 1 | 0 | 1 |
| *V. minicus* | 2 | 1 | 1 |
| *V. natriegens* | 1 | 0 | 1 |
| *V. ordalii* | 1 | 0 | 1 |
| *V. pelagius* | 1 | 0 | 1 |
| *V. ponticus* | 1 | 0 | 1 |
| *V. salmonicida* | 1 | 0 | 1 |
| *V. tubiashii* | 3 | 0 | 3 |
| *V. vulnificus* | 9 | 0 | 9 |
| Aeromonas[a] | 7 | 0 | 6 |
| Citrobacter | 1 | 0 | 1 |
| Enterobacter | 1 | 0 | 1 |
| Escherichia | 3 | 0 | 3 |
| Photobacterium | 1 | 0 | 1 |
| Plesiomonas | 1 | 0 | 1 |
| Proteus | 3 | 0 | 3 |
| Psuedomnas | 2 | 0 | 2 |
| Salmonella[a] | 6 | 0 | 6 |
| Serratia | 1 | 0 | 1 |
| Shigella | 3 | 0 | 3 |
| Staphylococcus | 7 | 0 | 7 |
| Yersinia | 3 | 0 | 3 |

[a]Autoafflutination was found.

Sensitivity, Specificity, False-Positive Reactions and False-Negative Reactions Sensitivity, specificity, false-positive reactions and false-negative reactions were determined as described by McClure (12), which reference is incorporated by reference. Sensitivity was defined as the number of test positives of *V. parahaemolyticus* (i.e. true positives) divided by the total strains of *V. parahaemolyticus* tested. Specificity was defined as the number of test negatives of non-*V. parahaemolyticus* (true negatives) divided by the total number of these bacterial strains tested. The false-positive rate was the percentage of test positives of non-*V. parahaemolyticus* divided by the total number of positive tests (misclassified positives plus true positives).

The false-negative rate was the percentage of test negatives of *V. parahaemolyticus* divided by the total number of negative tests (misclassified negatives plus true negatives). Strains showing uninterpretable results were not included in the calculation of performance.

The overall performance is shown in Table 2. Of the 94 isolates of *V. parahaemolyticus* tested, 93 isolates demonstrated positive reactions by the latex agglutination test of the invention, with only 1 strain being negative; therefore, the false-negative rate was 1.4% (1/73) (Table2). The sensitivity of the agglutination test was 98.9% (93/94). Of the 40 strains of Vibrio spp. other than *V. parahaemolyticus*, only 3 strains (one strain belonging to each species of *V. alginolyticus*, *V. harveyi* and *V. mimicus*) were positive; therefore, the false-positive rate is 3.1% (3/96). There were two strains of *V. cholerae* and *V. fischeri* which gave uninterpretable results (agglutination with control latex). Based on these results, the specificity of the latex agglutination of the invention for vibrios other than *V. parahaemolyticus* was 92.1% (35/38). Of the 39 strains (33 species) of non-vibrio bacteria tested, none gave positive reactions. Therefore, the specificity for non-vibrios was 100%, although there were 2 strains giving uninterpretable reactions.

TABLE 2

Summary of performance of latex agglutination test

| Bacteria | No. of strains | | | | Sensi-tivity[b] % | Specifity[b] % |
|---|---|---|---|---|---|---|
| | Total | Positive | Negative | U[a] | | |
| Vibrio parahaemolyticus | 94 | 93 | 1 | 0 | 98.9 | |
| Vibrio spp. | 40 | 3 | 35 | 2 | | 92.1 |
| Other bacteria | 39 | 0 | 37 | 2 | | 100.0 |

[a]Uninterpretable result was due to autoagglutination.
[b]Uninterpretable results were excluded from calculation of performance.

While only one embodiment of the present invention has been shown and described herein, it will be appreciated that modifications thereof, some of which have been alluded to hereinabove, may still be readily made thereto by those skilled in the art. We, therefore, intend by the appended claims to cover the modifications alluded to herein as well as all other modifications which fall within the true spirit and scope of our invention.

BIBLIOGRAPHY

1. Chang, T. C., S. Y. Tsai and H. C. Chen, 1991, ROC (Taiwan) Patent Application No. 79109870, Patent No. NI-50873.

2. Chang, T. C. and S. H. C. Ding, 1992, Rapid detection of *Staphylococcus aureus* in food by flow cytometry. *J. Rapid Methods Automation Microbiol.* 1:133–147.

3. Fuerst, J. A. and J. W. Perry, 1988, Demonstration of lipopolysaccharide on sheathed flagella of *Vibrio cholerae* 0:1 by protein A-gold immunoelectron microscopy. *J. Bacteriol.* 170:1488–1494.

4. Higgins, R. C. and M. E. Dahmus, 1979, Rapid visualization of protein bands in preparative SDS-polyacrylamide gels. *Anal. Biochem.* 93:257–260.

5. Hudson, L. and F. C. Hay, 1989, Affinity techniques for molecules and cells. "Practical Immunology" 3rd ed., pp. 322–329, Blackwell Scientific Publications, London.

6. Joseph, S. W., R. R. Colwell and J. B. Kaper, 1983, *Vibrio parahaemolyticus* and related halophilic vibrios. *CRC Crit. Rev. Microbiol.* 10:77–124.

7. Kabir, S., 1980, Composition and immunological properties of outer membrane proteins of *Vibrio cholerae*. *J. Bacteriol.* 144:382–389.

8. Kabir, S. 1986, Composition and immunological properties of the cell surface proteins of *Vibrio cholerae*. *J. Gen. Microbiol.* 132:2235–2242.

9. Koga, T. and T. Kawata, 1983, Isolation and characterization of the outer membrane from *Vibrio parahaemolyticus*. *J. Gen. Microbiol.* 129:3185–3196.

10. Linn, T. G., A. L. Greenleaf, R. G. Shorenstein, and R. Losick, 1973, Loss of the sigma activity of RNA polymerase of *Bacillus subtilis* during sporulation. *Proc. Natl. Acad. Sci. USA.* 70:1865–1869.

11. Lowry, O. H., N. J. Rosebrough, A. L. Farr, and R. J. Randall, 1951, Protein measurement with the Folin phenol reagent. *J. Biol. Chem.* 193:265–275.

12. McClure, F. D., 1990, Design and analysis of quantitative collaborative studies: minimum collaborative program. *J. Assoc. Off. Anal. Chem.* 73:953–960.

13. Weintraub, M., and S. Raymond, 1963, Antiserums prepared with acrylamide gel used as adjuvant. *Science* 142:1677–1678.

What is claimed is:

1. A method for rapid identification of *Vibrio parahaemolyticus* in a sample containing suspect colonies which comprises the steps of:
   (i) coating latex particles with a solution of antibodies or antisera against two outer membrane proteins of *V. parahaemolyticus* with molecular weights of 36,000 and 34,000, respectively, at a concentration effective to agglutinate *V. parahaemolyticus* in a sample so as to obtain a latex reagent, and
   (ii) mixing said sample containing suspect colonies with said latex reagent obtained in step (i) under conditions appropriate to complete agglutination, wherein the presence of agglutination identifies the presence of *V. parahaemolyticus* in said sample.

2. A kit for rapid identification of *V. parahaemolyticus* comprising latex particles coated with antibodies or antisera raised by immunizing animals with the mixture or either one of the two outer membrane proteins of *V. parahaemolyticus* with molecular weights of 36,000 and 34,000, respectively, and devices required for performing a latex agglutination test.

* * * * *

UNITED STATES PATENT AND TRADEMARK OFFICE
CERTIFICATE OF CORRECTION

PATENT NO. : 5,418,140
DATED : May 23, 1995
INVENTOR(S) : Chang et al.

It is certified that error appears in the above-indentified patent and that said Letters Patent is hereby corrected as shown below:

Item [73], Assignee : after "Institute" insert --Hsinchu, Taiwan--.

Item [57], Abstract, line 9, substitute --step-- for "the".
Column 2, line 19, substitute --1-3-- for "13-3".
Column 3, line 4, after "utilizes the" insert --antibodies--.
Column 3, line 53, substitute --of-- for "Of".
Column 3, line 54, substitute --known-- for "know".
Column 7, line 30, after "TWEEN" delete "TM".
Column 7, line 37, substitute --V. cholerae-- for "V. cholerae".
Column 7, line 46, substitute --34, 000-- for "34,000".
Column 8, line 48, (in the table, column 4), substitute --6-- for "5".
Column 8, line 52, (under the table), substitute --Autoagglutination-- for "Autoafflutination".
Column 9, line 12, substitute --Vibrio-- for "Vibrio".

Signed and Sealed this

Sixteenth Day of July, 1996

Attest:

BRUCE LEHMAN

Attesting Officer    Commissioner of Patents and Trademarks